United States Patent [19]
Petter et al.

[11] Patent Number: 5,902,742
[45] Date of Patent: May 11, 1999

[54] COMPLEX GROWTH SUPPLEMENT FOR MAINTENANCE OF BACTERIAL CELL VIABILITY AND INDUCTION OF BACTERIAL CELL DIFFERENTIATION

[75] Inventors: Jean Guard Petter, Athens; Kim D. Ingram, Watkinsville, both of Ga.

[73] Assignee: The United States of America as represented by the Secretary of Agriculture, Washington, D.C.

[21] Appl. No.: 08/649,501

[22] Filed: May 17, 1996

[51] Int. Cl.$^6$ .............................. C12N 1/20; C12N 1/00
[52] U.S. Cl. .................. 435/252.1; 435/243; 435/252.8; 435/253.6
[58] Field of Search ................................. 435/243, 245, 435/252.1, 253.6, 260, 879, 252.8

[56] References Cited

U.S. PATENT DOCUMENTS 5,510,241   4/1996   Thorns ..................................... 435/7.3

OTHER PUBLICATIONS

Petter et al., *Appl. Environ. Microb.*, vol. 61(8), pp. 2845–2851 (1995).
Petter, J., *Appl. Environ. Microb.*, vol. 59(9), pp. 2884–2890 (1993).
Petter, J., *Abstracts of the 96th General Meeting of the American Society for Microbiology*, p. 252 (May 19–23, 1996).
Ibrahim et al., *J. Food Protection*, vol. 49(2), pp. 92–98 (1986).
MacNab et al., *Annu. Rev. Genet.*, vol. 26, pp. 131–158 (1992).
Schnaitman et al., *Microb. Reviews*, vol. 57(3), pp. 655–682 (1993).
Kilger et al., *J. Clinical Microb.*, vol. 31(5), pp. 1108–1110 (1993).
Reeves, P., *TIG*, vol. 9(1), pp. 17–22 (1993).
*DIFCO Manual*, Tenth Edition, pp. 772–837 (1984).
*DIFCO Manual*, Tenth Edition, pp. 163–456 (1984).
Hinton et al., *Mol. Microb.*, vol. 1(3), pp. 381–386 (1987).
Fraser et al., *Proc. Natl. Acad. Sci.*, vol. 75(12), pp. 5936–5940 (1978).
Sloan et al., *J. Biol. Chem.*, vol. 269(44), pp. 27625–27630 (1994).
Stratford et al., *Microbiology*, vol. 140, pp. 2657–2662 (1994).
Hansen, T., *Antonie van Leeuwenhoek*, vol. 66, pp. 165–185 (1994).
Tam et al., *Microb. Reviews*, vol. 57(2), pp. 320–346 (1993).
Newton et al., *J. Bacter.*, vol. 175(9), pp. 2734–2742 (1993).
Sachsenweger et al., *Tierärztl Prax*, vol. 22, pp. 350–357 (1994).
Holt et al., *J. Food Prot.*, vol. 58(9), pp. 967–972 (1995).
Stanley et al., *Mol. Microb.*, vol. 10(4), pp. 781–787 (1993).
Parker et al., *J. Bacter.*, vol. 174(8), pp. 2525–2538 (1992).
Raha et al., *J. General Microb.*, vol. 139, pp. 1401–1407 (1993).
Park et al., *J. Bacter.*, vol. 177(21), pp. 6255–6262 (1995).
Storz et al., *Symposium: Regulation of Antioxidant Enzymes*, pp. 627–673 (1992).
Wilson et al., *Mol. Microb.*, vol. 19(5), pp. 1025–1034 (1996).
Ferrante et al., *Proc. Natl. Acad. Sci.*, vol. 92, pp. 7617–7621 (1995).
Bruchhaus et al., *Mol. Bioc. Paras.*, vol. 70, pp. 187–191 (1995).
Armstrong–Buisserct et al., *Microbiology*, vol. 141, pp. 1655–1661 (1995).
Tsuji et al., *Biochem. J.*, vol. 307, pp. 377–381 (1995).
Chae, J., *Biol. Chem.*, vol. 269(44), pp. 27670–27678 (1994).
Tartaglia et al., *J. Biol. Chem.*, vol. 265(18), pp. 10535–10540 (1990).
Mercer et al., *Biot. Bioeng.*, vol. 42, pp. 1277–1286 (1993).
Budrene et al., *Nature*, vol. 376(6), pp. 49–53 (1995).
Titgemeyer, F., *J. Cell. Bioc.*, vol. 51, pp. 69–74 (1993).
Ogasawara et al., *Biol. Pharm. Bull.*, vol. 18(8), pp. 1045–1048 (1995).
Das et al., *Fems Microb. Letters*, vol. 112, pp. 67–72 (1993).
Humphrey et al., *Epidemiol. Infect.*, vol. 106, pp. 489–496 (1991).
Sand et al., *Appl. Microb. Biot.*, vol. 43, pp. 961–966 (1995).
Shivaprasad et al., *Avian Diseases*, vol. 34, pp. 548–557 (1990).
Allison et al., *Infection Immunity*, vol. 60(11), pp. 4740–4746 (1992).
Harshay et al., *Proc. Natl. Acad. Sci.*, vol. 91, pp. 8631–8635 (1994).
St. Louis et al., *JAMA*, vol. 259(14), pp. 2103–2107 (1988).
Simonen et al., *Microb. Reviews*, vol. 57(1), pp. 109–137 (1993).
Gennity et al., *Current Opinion in Biotechnology*, vol. 2, pp. 661–667 (1991).
Mishu et al., *J. Infect. Dis.*, vol. 169, pp. 547–552 (1994).
Chart et al., *Epidemiol. Infect.*, vol. 104, pp. 63–71 (1990).
Barrow et al., *Avian Diseases*, vol. 36, pp. 227–236 (1992).
Petter et al. 95th General Meeting of the ASM. May 21–25, 1995. Abstract.

(List continued on next page.)

*Primary Examiner*—Leon B. Lankford, Jr.
*Assistant Examiner*—Christopher R. Tate
*Attorney, Agent, or Firm*—M. Howard Silverstein; John Fado; Gail E. Poulos

[57] ABSTRACT

A growth supplement for bacterial media is used to induce and/or maintain differentiation and viability of bacterial cell cultures. The supplement contains about 10 mM to about 100 mM of a sugar, an amino acid or mixtures thereof. When the media used does not contain iron and reducing agents, such as sodium thiosulfate, these are included in the supplement. The reducing agent is present preferably at about 20 to about 40 mM. The addition of this supplement results in flagellation of aflagellate variants of Salmonella and hyperflagellation of variants of Salmonella which are flagellated.

7 Claims, 14 Drawing Sheets

OTHER PUBLICATIONS

Harshey et al. PNAS. vol. 91, pp. 8631–8635, 1994.
Miake et al. Microbiol. and Immunol. vol. 39(7), pp. 437–442, Abstract enclosed, 1995.
Miller et al. J. Food Protect. vol. 58(1), pp. 115–119, 1995.
Sobeh et al. Indian J. Med. Res. vol. 78, pp. 170–176, Abstract enclosed, 1983.
Harshey, R. Mol. Microbiol. vol. 13(3), pp. 389–394, 1994.
McFaddin, J. Biochemical Tests for Identification of Medical Bacteria. pp. 162–167, 1980.
Smith et al. Microbiology. vol. 141(7), pp. 1739–1744, Abstract enclosed, 1995.
Marie et al. Hoppe–Seylers Z. Physiol. Chem. vol. 361, pp. 603–606, 1980.

Schlecht et al. Zentralblatt fuer Bakteriol. vol. 281(1), pp. 30–37, Abstract enclosed, 1994.

Aleksandrov et al. Vaktsiny Syvorotki. No. 5, pp. 20–28, Abstract enclosed, 1965.

Evans et al. Curr. Microbiol. vol. 23(2), pp. 71–74, Abstract enclosed, 1991.

Valone et al. Infect. Immun. vol. 61(2), pp. 705–713, Abstract enclosed, 1993.

Tkachenko et al. Mikrobiol. vol. 45(3), pp. 450–454, Abstract enclosed, 1976.

Rappold et al. Appl. Environ. Microbiol. vol. 39(1), pp. 162–163, 1979.

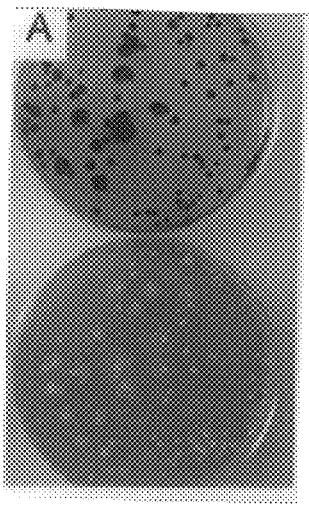
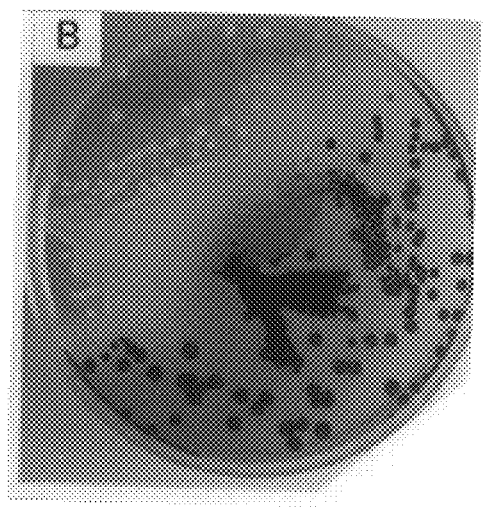
Fig. 2a          Fig. 2b
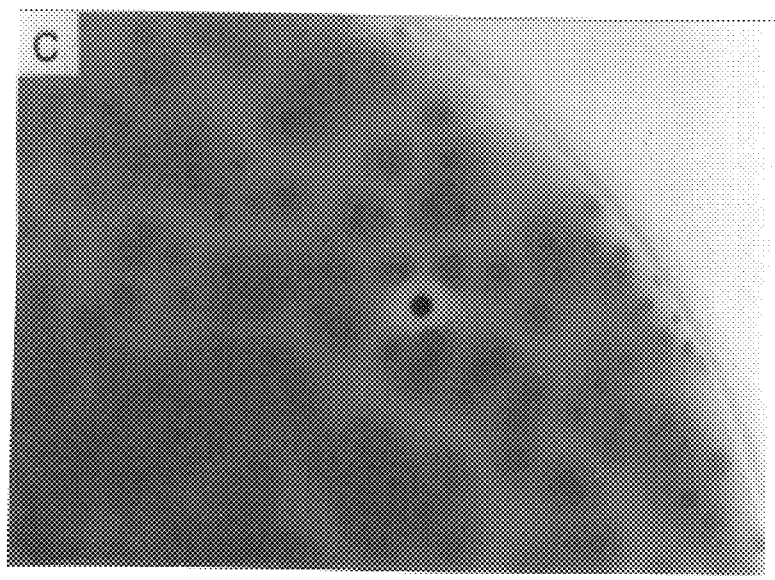
Fig. 2c

COMPLEX GROWTH SUPPLEMENT FOR MAINTENANCE OF BACTERIAL CELL VIABILITY AND INDUCTION OF BACTERIAL CELL DIFFERENTIATION

BACKGROUND OF THE INVENTION

1. Field of the Invention

This invention relates to a growth supplement for culture medium for the maintenance of cell viability and for the induction of differentiation, especially of bacterial cells. It also relates to a method for growing cells, especially enteric bacteria such as variants of *Salmonella enterica*, for the production of biologics, such as vaccines, assays and the enhancement of protein secretion in general.

2. Description of the Prior Art

A medium which induces cell differentiation in both prokaryote and eukaryote cells will aid in understanding neoplasia, birth defects, regeneration of nervous system function after debilitating accidents, development of artificial models for diseases such as Alzheimer's disease and diabetes, as well as the production of improved vaccines to infectious disease agents and identification of contamination of animal products that are a part of the human food supply.

For example, rapid and reliable detection of Salmonella serotypes is important for determining the presence of Salmonella in food and animals, such as for example, chickens used for egg production. Standard methods for Salmonella detection are often not sensitive enough to consistently detect the presence of Salmonella serotypes in all instances. Fowl salmonellosis caused by *Salmonella enterica* var. Gallinarum and Pullorum are diseases of world wide significance in the poultry industry. Since its recognition as an infectious agent nearly 100 years ago, *Salmonella enterica* var. Pullorum has been classified as a non-motile, aflagellate chicken pathogen (Retter, N.Y. Med. J., Volume 71, 803,1990; Edwards et al, Identification of Enterobacteriaceae, Burgess Publishing Company, Minneapolis, Minn., 1962). It is particularly capable of contaminating eggs via the reproductive organs of hen (Snoeyenbos, Diseases of Poultry, ninth edition; Ed.: B. W. Calnek; 73–86, 1991). In the United States, *S. enterica* var. Pullorum was a major problem in the poultry industry earlier this century. The problem decreased following implementation of rigorous serological screening and depopulation of serologically positive flocks. Serological surveillance has been the primary method of keeping *S. enterica* var. Pullorum in check. However, problems have begun to erupt in a number of United States flocks and indications are that the standard tests for *S. enterica* var. Pullorum, such as the agglutination assays, are not detecting some infected flocks. Currently, *S. enterica* var. Enteritidis is the cause of a world-wide increase of salmonellosis in people due to its ability to colonize the reproductive organs of chickens and to contaminate eggs. *S. enterica* var. Enteritidis has the same lipopolysaccharide (LPS) D1 serotype as *S. enterica* var. Pullorum, but it is commonly flagellated and produces flagellar H-antigens that are used in a diagnostic scheme to differentiate it from other salmonellae (Edwards, supra). Glycosylated, high-molecular weight (HMW) O-antigen distinguishes virulent strains (Petter, Appl. Env. Microbiol., Volume 59, 2884–2890, 1993; Guard-Petter et al, Appl. Env, Microbiol., Volume 61, 2845–2851, 1995; Guard-Petter et al, Epid. Infec., 1996, In Press; R. Carlson, personal communication). This type of O-antigen structure contributes to the ability of *S. enterica* var. Enteritidis to hyperflagellate and migrate across a 2% agar surface, but this distinctive phenotype is transient and is lost upon passage and storage (Guard-Petter et al, 1995, supra; Guard-Petter et al, 1996, supra). Hyperflagellation has been described as an outer membrane change that occurs with the differentiation of vegetative bacteria into swarm cells (Allison et al, Molec. Microbiol., Volume 169, 1155–1158, 1994; Allison et al, Infec. Immun., Volume 60, 4740–4746, 1992). A genetic analysis of *E. coli* and *S. enterica* var. Typhimurium indicated that swarm cell differentiation could be observed in soft agar (Harshay et al, PNAS, USA, Volume 91, 8631–8635, 1994). A correlation between differentiation and virulence has been described for the urinary tract pathogen *Proteus mirabilis* (Allison et al, 1994, supra; Allison et al, 1992, supra) where other virulence factors such as toxins and metalloproteases are transcriptionally upregulated at the same time as flagellin. To date, a relationship between virulence and hyperflagellation for *S. enterica* var. Enteritidis has been made only in those strains that swarm on 2% agar surfaces, because even avirulent rough and semismooth strains of *S. enterica* var. Enteritidis produce flagella and are motile in soft agar (Guard-Petter et al, 1996, supra). These emerging concepts suggest that at least some aspects of swarm cell differentiation might be involved in the ability of *S. enterica* var. Enteritidis to contaminate eggs. However, evidence against an association between swarm cell differentiation and egg contamination exists. *S. enterica* var. Pullorum efficiently contaminates eggs while *S. enterica* var. Enteritidis does so sporadically (Snoeyenbos, 1991, supra; Shivaprasad et al, Avian Dis., Volume 34, 548–557, 1990; Humphrey et al, Epidemiol. Infect., Volume 106, 489–496, 1991; Keller et al, Infec. Immun., Volume 63, 2442–2449, 1995). Since *S. enterica* var. Pullorum is historically aflagellate it was considered that either a) the ability to flagellate and undergo swarm cell differentiation was not involved in establishing invasive infections, or b) cellular differentiation of *S. enterica* var. Pullorum was inhibited.

U.S. Pat. No. 5,510,241 (Thorns) discloses that Salmonella microorganisms produce fimbrial antigens when they grow in vivo, e.g. in the gut, in animal tissues or fluids, in food products and in some natural environments but many of the fimbral antigens are not produced when they are grown in vitro on most culture media. The patent also discloses a medium for inducing Salmonella, such as for example *S. enteritidis* and *S. dublin*, to produce a specific fimbrial antigen during in vitro culture so that fast and very specific assays can be performed. The media identified by the Thorns patent, useful for inducing a specific fimbrial antigen, SEFA, on serotypes *S. enteritidis* and *S. dublin*, are media having at least 20% by weight of their nutrient composition made up of "defined" nutrients which are inorganic salts and/or organic compounds of known molecular structure. Peptone water and Enriched E broth are given as examples of preferred liquid media, with Slanetz broth, Heart infusion broth and Vogel Bonner broth as media capable of supporting expression of the specific antigen. The patent discloses, as examples of solid media, desoxycholate citrate agar, McConkey agar, Nutrient agar, Salmonella Shigella agar, Sheep blood agar and Xylose Lysine descholate. Oxoid Isosensitest and Sensitest agars are disclosed as those which are more potent in supporting the expression of the antigen.

Existing medias do not supply bacteria with essential ingredients that enable them to display a full range of potential physiological behavior in vitro. There remains a need in the art for more effective media which maintains cell viability and induces differentiation. The present invention described below is a growth supplement for media which induces and/or maintains differentiation and maintains viability of cells, especially bacterial cells and is different from prior art media.

SUMMARY OF THE INVENTION

It is therefore an object of the present invention to provide a growth supplement for culture medium for growing cells that maintains cell viability and induces differentiation.

Another object of the present invention is to provide a growth supplement for a bacterial culture medium for maintaining cell viability and for inducing differentiation of bacterial cells.

A further object of the present invention is to provide a growth supplement for a bacterial culture medium capable of inducing cell surface antigens on bacterial cells.

Another object of the present invention is to provide a growth supplement for bacterial culture media wherein the supplement contains a metabolite of either a sugar, an amino acid or mixtures thereof in amounts to induce or maintain differentiation and viability of the cells in culture.

A still further object of the present invention is to provide a growth supplement for bacterial culture medium wherein the supplement contains a metabolite of either glucose, maltose, proline, N-acetylglucosamine, glucosamine, glutamine and mixtures thereof for growing enteric bacteria.

Another object of the present invention is to provide a growth supplement for bacterial culture medium wherein the metabolite in the supplement has a final concentration of approximately 1 mM to approximately 100 mM of either glucose, maltose, proline, N-acetylglucosamine, glucosamine, glutamine and mixtures thereof in the medium.

A further object of the present invention is to provide a growth supplement for a bacterial culture medium wherein the metabolite in the supplement has a final concentration of approximately 1 mM to approximately 40 mM of either glucose, maltose, proline, N-acetylglucosamine, glucosamine, glutamine and mixtures thereof in the medium.

Another object of the present invention is to provide a growth supplement for a bacterial culture medium wherein the metabolite in the supplement has a final concentration of approximately 5 mM to approximately 10 mM of either glucose, maltose, proline, N-acetylglucosamine, glucosamine, glutamine and mixtures thereof in the medium.

A further object of the present invention is to provide a method for inducing differentiation of bacterial cells using a medium supplemented with either glucose, maltose, proline, N-acetylglucosamine, glucosamine, glutamine and mixtures thereof.

Further objects and advantages of the present invention will become apparent from the following description.

BRIEF DESCRIPTION OF THE DRAWINGS

FIGS. 1A and 1C are *S. enterica* vars. Pullorum and Enteritidis, respectively, grown without supplementation. FIGS. 1B and 1D are *S. enterica* vars. Pullorum and Enteritidis, respectively, grown with 100 mM glucose on 1.4% HEA media for 40 hours for Pullorum and 16 hours for Enteritidis. FIGS. 1D and 1E show that bundled structures on *S. enterica* var. Enteritidis composed primarily of flagellin are evident. FIG. 1F shows hyphae production by *S. enterica* var. Enteritidis. Hyphae extend beyond the edge of the colony and turn agar opaque. FIG. 1G show *S. enterica* var. Enteritidis grown with 100 mM Glutamine. FIG. 1H shows *S. enterica* var. Enteritidis grown with 100 mM N-acetylglucosamine. FIG. 1I shows *S. enterica* var. Enteritidis grown with 100 mM proline. FIG. 1J shows *S. enterica* var. Enteritidis grown with 100 mM proline and 100 mM N-acetylglucosamine. FIG. 1K shows *S. enterica* var. Enteritidis grown with 100 mM glutamine and 100 mM N-acetylglucosamine. Scale bar at the upper left corner of FIG. 1A is 1 μm and is the same for FIGS. 1B–1K. FIG. 1E is reduced 33%.

FIGS. 2A–2C are photographs of glucose supplemented *S. enterica* var. Enteritidis at different concentrations of glucose supplementation. FIG. 2A shows that using 10 mM glucose produces black colonies (top) and 100 mM glucose produces yellow/orange colonies (bottom; shown as light color colonies in black and white photograph). FIG. 2B shows that using 50 mM glucose produces mixed patterns of black and yellow colonies if air passes over the plate surface. FIG. 2C shows a stable mutant black colony phenotype as identified on screening plates of HEA supplemented with 100 mM maltose after chemical mutagenesis with MNNG. The opaque area between colonies is due to flagella permeating the agar between colonies while agar around mutant remains clear.

(FIG. 4A) H-antigen reactive cell surface material. Lanes 1–3: Typhimurium LT2, 100 mM glucose; rough Enteritidis, 10 mM maltose; and Pullorum, 100 mM glucose. Arrows indicate 60, 54 and 50 kDa form top to bottom. (FIG. 4B) D1 O-antigen reactive cell surface material. Lanes 1 and 2, serovar B Typhimurium LT2, 100 mM glucose; Lanes 3 and 4, serovar D1 Enteritidis, 10 mM maltose; Lanes 5 and 6, rough Enteritidis, 100 mM maltose. A(+) indicates samples that were hydrolyzed with bacteriophage P22 endorhamnosidase to specifically remove free O-antigen in order to improve visualization of the 50 kDa flagellin isotype that is cross-reactive with the D1 antiserum (Difco) used as primary antibody.

DETAILED DESCRIPTION OF THE INVENTION

Figure 1A:
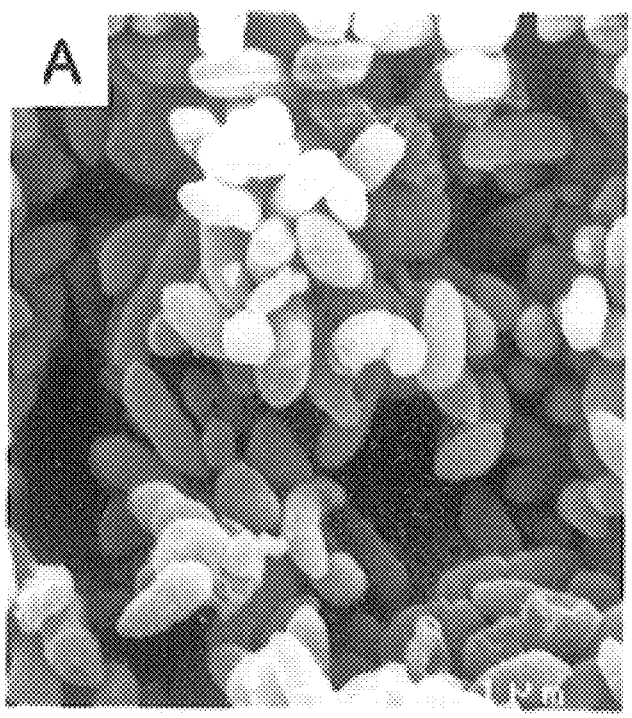
FIGS. 1A–1K are scanning electron micrographs of *S. enterica* vars. Pullorum and Enteritidis before and after glucose supplementation.

The importance of enteric infections in humans has been increasingly well recognized over the last dozen years. The relationship of poultry contamination and human infection has, likewise, become well documented. It is important to be able to accurately test for the presence of enteric bacteria and to be able to prevent the occurrence of these bacteria in the human food chain. In order to achieve this, culture media are needed which consistently maintain and/or induce a differentiated morphology. The development of a growth supplement for culture media which induces and/or maintains a differentiated morphology will aid in 1) the production of improved killed bacterial vaccines for all animal species, 2) the development of modified live bacterial vaccines for all animal species and 3) the production and recovery of engineered proteins, either prokaryote or eukaryote, from bacterial expression systems.

The inventors suggest that metabolite supplementation of bacterial culture media results in patterns of gene expression that overlap with genes important in chemotaxis (Titgemeyer, J. Cell Biochem., Volume 51, 69–74, 1993; Budrene et al, Nature, Volume 376, 49–53, 1995; Mercer et al, Biotechnology and Bioengineering, Volume 42, 1277–1286, 1993; and McCleary et al, J. Biol. Chem., Volume 269, 31567–31572, 1994). For example, chemotaxis might provide the function of "reading" the environment, while metabolite concentration is the signal to "turn the page" and differentiate. Thus, a close association of the two processes is likely required for bacteria to achieve differentiation.

It has been discovered that supplementation of bacterial culture media with metabolites such as sugars and amino acids; for example, glucose, maltose, proline, N-acetylglucosamine, glucosamine, glutamine and mixtures thereof, induces copious secretion of proteins, changes in colony morphology and cell shape. The concentrations of these simple metabolites appears to be the environmental signal used by bacteria to induce differentiation. In order to improve survival of cells upon exposure to the inducing signal, media is furter modified as will be described below.

The media of this invention is applicable to any cell, particularly bacterial cells. Such bacteria include, but are not limited to, species of bacteria from the genera Salmonella, Escherichia, Shigella, Vibrio, Enterobacter and Campylobacter. Examples of specific bacteria are varients of *Salmonella enterica*, for example, Enteritidis, Pullorum, Typhimurium, Schwarzengund, etc.

The term growth supplement means any supplement for culture media which induces and/or maintains differentiation and viability of bacteria. Differentiation means the production and secretion of proteins across the cell membrane that results in at least about a three-fold enhancement. Hypersecretion, including hyperflagellation, is included in the definition of differentiation and is defined as at least about a ten-fold enhancement of protein recovered in comparison to avirulent Salmonella Enteritidis SE6-E21 and SE6-E5. The growth supplement contains either a sugar, an amino acid or mixtures thereof in concentrations that induce differentiation. Examples of sugars useful in the present invention include glucose, maltose, N-acetylglucosamine, galactose, rhaminose, sialic acid, etc. Any sugar that has specific and non-specific transport pathways are useful in the present invention. Preferred sugars include glucose, glucosamine, N-acetylglucosamine and maltose. Examples of amino acids useful in the present invention include proline, glutamine, asparagine, etc. Other amino acids that have specific and non-specific transport pathways are useful in the present invention. Preferred amino acids are proline and glutamine. Sugars and amino acids with known transport systems yield positive results while sugars such as sucrose, lactose, and glycerol yield negative results. The important factor is that the concentration of the sugars and amino acids, by themselves or in combination, is the inducing agent, and that specific concentrations produce different levels of differentation. The growth supplement of the present invention is added to any culture media useful for culturing bacterial cells such as common bacterial media used in molecular biology (In Molecular Cloning: A Laboratory Manual, Seabrook et al, EDS., Appendix A). These media include, for example, Hektoen Enteric Agar (HEA) (Difco, Detroit, Mich.), Brain Heart Infusion Broth (BHI) (Difco, Detroit, Mich.), Luria broth (Difco), etc.

Iron and reducing agents are added if the media used do not contain them. The term reducing agent means any reducing agent compatible with a cell culture medium, especially a bacterial cell culture medium. A preferred example is thiosulfate. Other examples are 2-mercaptoethanol, monothioglycerial, tetrahionate, and other sulfated compounds. Generally, the reducing agent is present in a concentration of about 1 mM to approximately 100 mM, with a preferred range of about 20 mM to about 40 mM. Iron includes ferric ammonium citrate, ferric ammonium sulfate, ferric chloride, ferric citrate and other soluble forms that support growth of bacteria. Ferric ammonium citrate is preferred. Iron is present in a concentration of about 1 mM to about 50 mM, with a preferred concentration of about 5 mM.

The sugars, amino acids, and mixtures thereof are added to the media using conventional techniques, to a final concentration of from approximately 1 mM to about 100 mM. A more preferred final concentration is from approximately 1 mM to about 40 mM. The two most preferred concentrations are about 10 mM and about 100 mM. For mixtures of supplements, these are added to a final concentration in a range of about 10 mM to about 100 mM each. Most mixtures are added at a final concentration of about 100 mM each. The most preferred mixture is about 100 mM maltose plus about 10 mM glucose.

The supplement is prepared and added to the media during media preparation using conventional techniques. The supplements are made up as 10X sterile solutions in sterile water. The solutions are filter sterilized or autoclaved when appropriate. For example, amino sugars are filter sterilized while glucose can be autoclaved.

The following examples are intended to further illustrate the invention and are not intended to limit the scope of the invention as defined by the claims.

EXAMPLE 1

*Salmonella entetica* vars. Enteritidis SE6-R, SE6-E5 and SE6-E21$^{Lacey}$ are recovered from the spleens of chicks or from hen eggs as previously described Petter, Appl. and Environ. Microbiol., Volume 59, 288 4–2890, 1993, herein incorporated by reference). Bacteria are also recovered from the spleens of mice as described for chicks. Other bacterial strains such as *E. coli* and other Salmonella serotypes are obtained from stock centers (K. Sanderson, Salmonellae Stock Center, Calgary, Calif.; National Veterinary Services Laboratory, Ames, Iowa), or as gifts from other investigators. Cam Greene, Southeast Poultry Research Laboratory, Agricultural Research Service, Athens, Ga., supplied the non-D1 serovars listed in Table 1 as well as several of the D1 strains. K. Lampel, FDA, 200 C Street, S.W., Washington, D.C. supplied *S. enterica* var. Berta; J. Roth, Department of Biology, University of Utah, Salt Lake City, Utah supplied *S. enterica* var. Typhimurium LT2. *S. enterica* var. Pullorum strains 1950, and 1268 as well as Pullorum/Gallinarum PC-CP5-5298E were obtained from the Maryland Department of Agriculture, Salisbury, Md. Phage type 4 isolates of *S. enterica* var. Enteritidis were obtained from the Center for Disease Control, Atlanta, Ga. All Salmonella strains are cultured for isolation and identification on Brilliant Green Agar (Difco, Detroit, Mich.). Other bacteria are cultured on selective media appropriate for their identification using standard microbiological techniques. Well-isolated bacterial colonies are passaged to brain heart infusion broth (BHI) (Difco) and are stabbed directly for storage into deep nutrient agar media contained in sterile tightly capped or corked tubes. Cultures are grown overnight for 16 hours at 37° C. to stationary phase. An exception is that Pullorum requires an additional 24 hours of growth. Salmonellae from birds are cultured at 42° C. which is the avian body temperature. Cultures are grown with aeration in 20×150 mm aluminum capped culture tubes. For storage at −70° C., 850 $\mu$l of overnight stationary phase cells are mixed with 150 $\mu$l presterilized glycerol in O-ring capped tubes. All storage conditions and techniques use standard microbiological procedures. Bacteria are recovered from nutrient agar stabs or from frozen glycerol stocks and are streaked onto appropriate agar media for evaluation of purity. They are then passaged to the agar or broth of interest. Preferred agar medias are brain heart infusion, brilliant green agar and hektoen enteric agar with and without supplementation. Preferred broth medias are Luria-Bertoni broth and brain heart infusion with or without supplementation and with or without aeration. All these media are available from Difco, except brilliant green which is obtained from BBL, Becton-Dickinson, Cockysville, Md.

EXAMPLE 2

Stationary phase cells of Enteritidis and Pullorum, grown 16 and 40 hours respectively, in brain heart infusion broth at 42° C. with no aeration, were plated onto supplemented 1.4% HEA. To achieve a colony density of 50 to 200 colonies per plate, 100 $\mu$l of a $10^7$ dilution of stationary phase cells at an optical density of about 0.9 to about 1.2 measured at a wavelength of 600 nm (A600) was spread on agar plates. Enteritidis cultures were plated for 16 hours, while Pullorum was incubated for a total of 40 hours. Pullorum cultures in general require twice the incubation time as that of Enteritidis. 1.4% Hektoen Enteric Agar (HEA) (Difco, Detroit, Mich.) is supplemented with 10 mM, 50 mM, 100 mM and 200 mM of glucose, maltose, lactose, sucrose, glycerol, N-acetylglucosamine, glucosamine, or glutamine in sterile water.

Colonies for scanning electron microscopy (SEM) are prepared based on a procedure designed to examine fungal agar cultures (Cole, Preparation of microfungi for SEM, 1986, In Ultrastructure techniques for microorganisms, Plenum Press, New York, N.Y.; herein incorporated by reference). Cultures are grown 16 hours (40 hours for Pullorum) at 37° C. on HEA with supplementation as described above. No difference was detected in cultures grown at 42° C. Sections of colonies were excised from agar plates with a thin layer of agar left attached, and after fixation, dehydration, critical point drying and sputter coating, sections were examined on a Philips 505 SEM.

Figure 3:
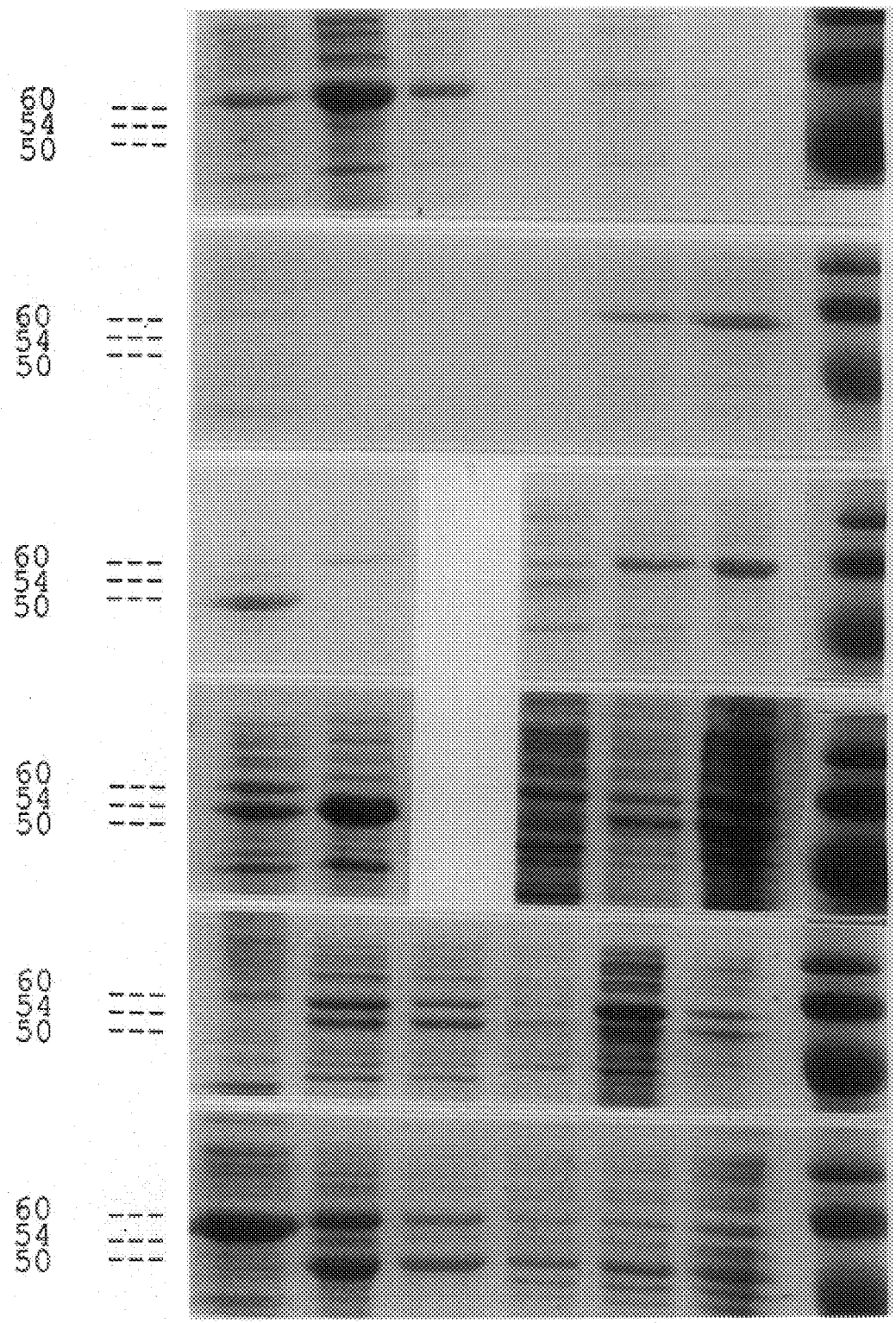
FIG. 3 is a photograph of a polyacrylamide gel showing flagellin isotypes as detected in coomasie stained polyacrylamide gels. 60, 54 and 50 kDa from top to bottom are indicated. Molecular weight markers (right most edge) are phosphorylase B (97.4 kDa). Bovine serum albumin (68 kDa) and ovalbumin (43 kDa). Cultures were supplemented as follows from Lane 1 to Lane 6: 10 mM glucose, 100 mM glucose, 200 mM glucose, 10 mM maltose, 100 mM maltose, 200 mM maltose. Cultures for lanes D3 and E3 (200 mM glucose) were not done. (A–C) Pullorum/Gallinarum strain PC CP5-5298E and Pullorum strains 1950 and 1268 (J. deGraft-Hanson and G. Stein, Maryland Department of Agriculture, Animal Health Department, P.O. Box J, Salisbury, Md. 21802); (D) smooth Enteritidis (J. Guard-Petter, Athens, Ga.); (F) Typhimurium LT2 (J. Roth, 201 S. Biology, Univ. Of Utah, Salt Lake City, Utah 84112).

Flagellin isotypes are recovered as described by Allison et al (Molec. Microbiol, Volume 169, 1155–1158, 1994, herein incorporated by reference) except that 50% ammonium sulfate is used for precipitation of protein rather than tricarboxylic acid. Cultures are grown as described above at 37° C. in brain infusion broth supplemented with 5 mM ferric ammonium citrate and 30 mM sodium thiosulfate and 10 mM glucose, 100 mM glucose, 200 mM glucose, 10 mM maltose, 100 mM maltose, or 200 mM maltose (FIG. 3).

Figure 1B:
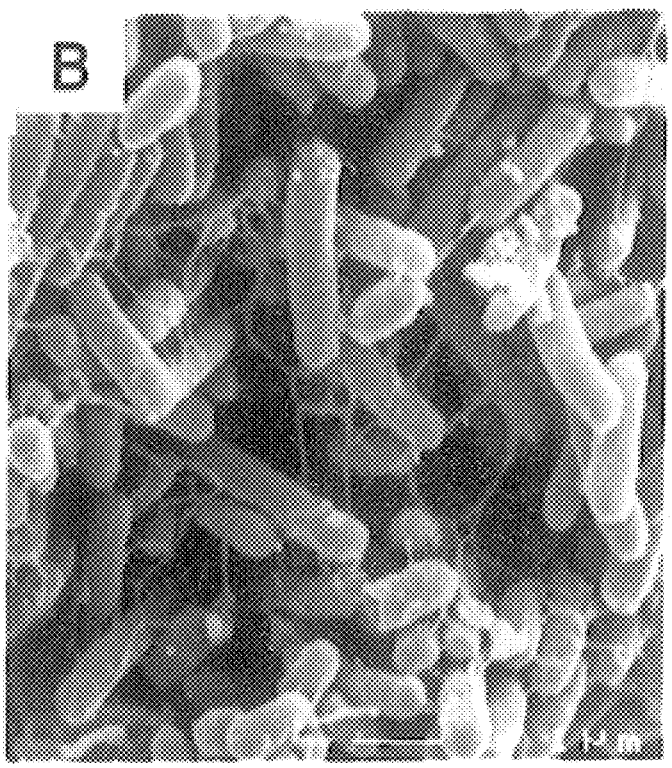
Figure 1C:
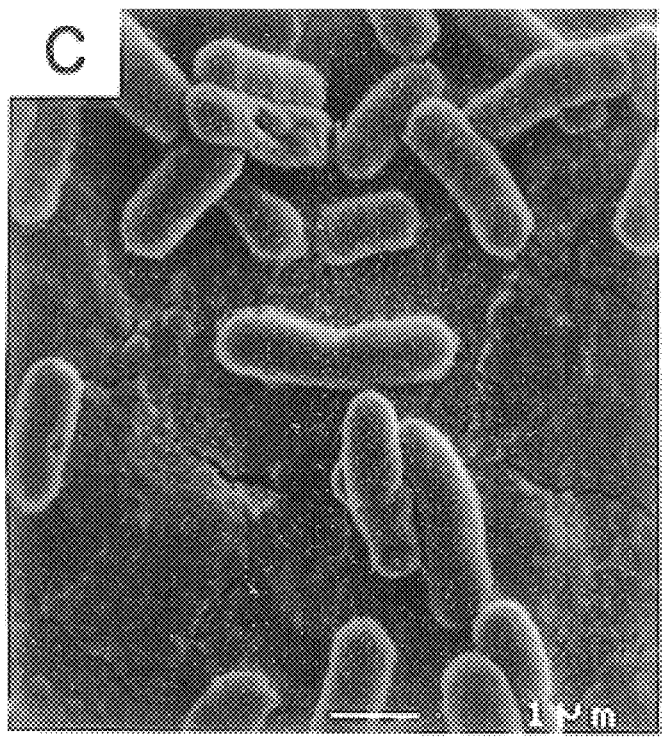
Figure 1D:
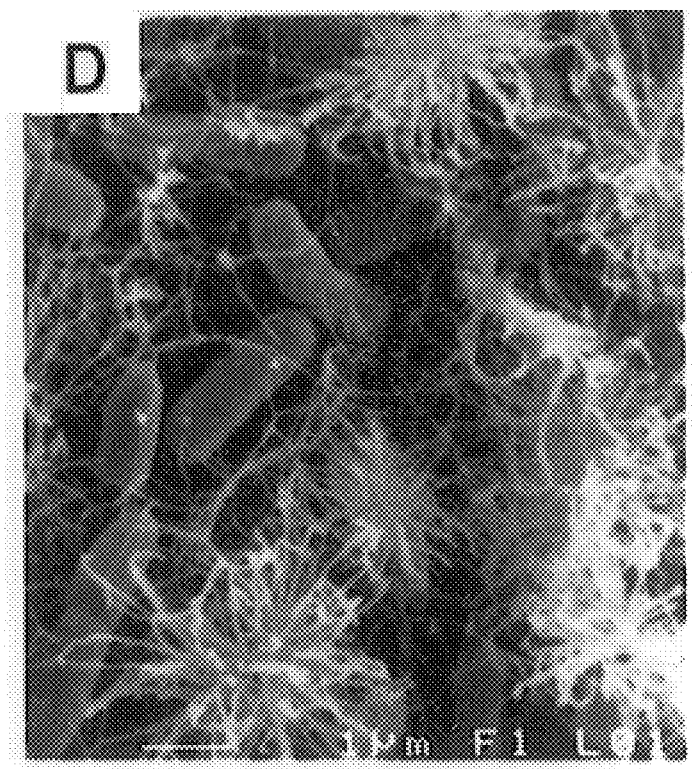
Figure 1E:
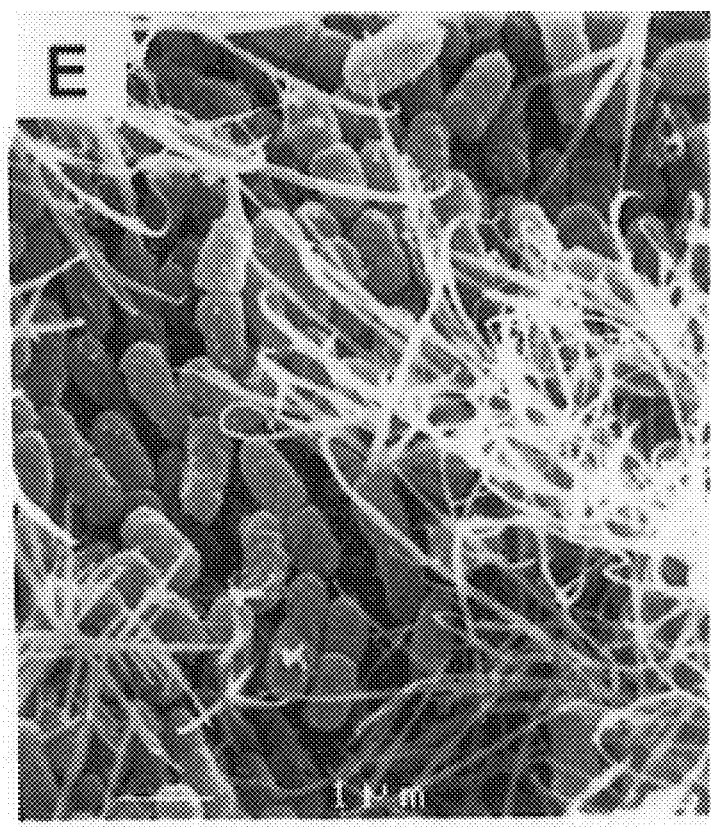
Figure 1F:
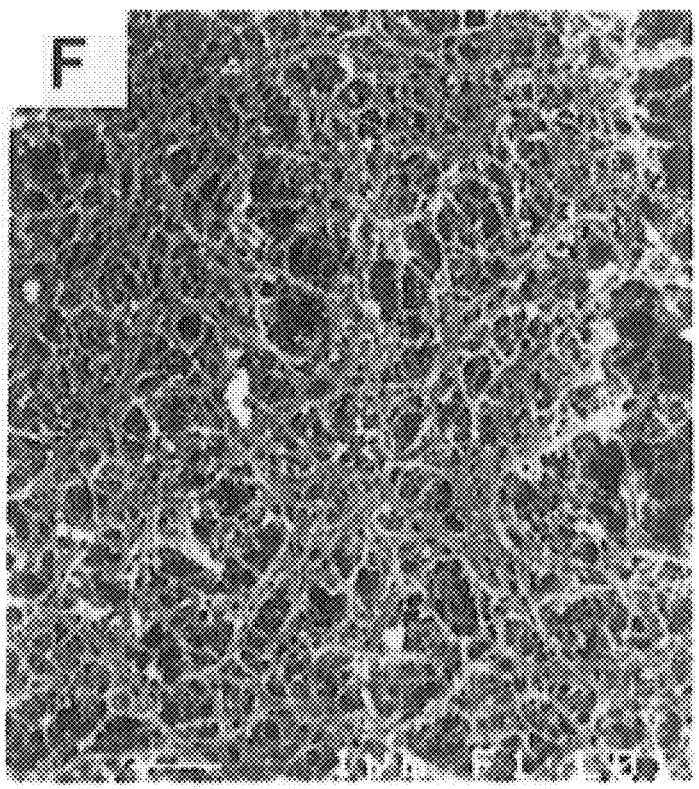

Metabolite supplementation results in enhanced recovery of flagella and increased colony mass for all Salmonella serovars examined to date (Tables 1 and 2 below). Lactose, sucrose and glycerol did not enhance surface flagellation. While a concentration of 10 mM significantly increases colony mass over that of unsupplemented HEA, a concentration of 100 mM induces differentiation as monitored by flagellation and a concurrent change in colony color. Supplementation with 10 mM of glucose, maltose, proline, N-acetylglucosamine, glucosamine or glutamine results in black colonies, supplementation with 50 mM results in a mixture of black and yellow colonies (FIGS. 1A and 1B). The concentration of metabolite at which the color change occurred was not a continuous gradient. Instead colonies remained black until at least a 50 mM concentration was available. Agar around yellow colors became opaque and rapidly progressed in areas where colony density was highest. SEM indicates that the cause of this opacity is a hyphae-like mesh that extends past the edge of such colonies (FIGS. 1C and 2F). Again, flagellin is the major protein recovered from the cell surface of such colonies. Black colonies repelled the hyphae-like structures emanating from yellow colonies. Chemical mutagenesis with MNNG to 50% cell survival was done to see if a mutant phenotype could be identified for further genetic investigations. Whereas a recurring mutant black phenotype that did not turn yellow upon supplementation was recovered (6 of 20,000 CFU screened) (FIG. 2C), all yellow colonies continued to produce hyphae. These results suggest that while the black to yellow colony color change is probably traceable to one or a few genes, the production of hyphae probably involves redundant genes. It is also possible that a complete knockout of hyphae production is lethal. Chemical mutagenesis produced mutants that would not differentiate upon supplementation which suggests that operons and genes associated with the black-to-yellow colony color change can be identified. Transposon mutagenesis which generates mainly single hit mutants has not yet resulted in a similar mutant phenotype (Hay et al, unpublished).

Figure 1G:
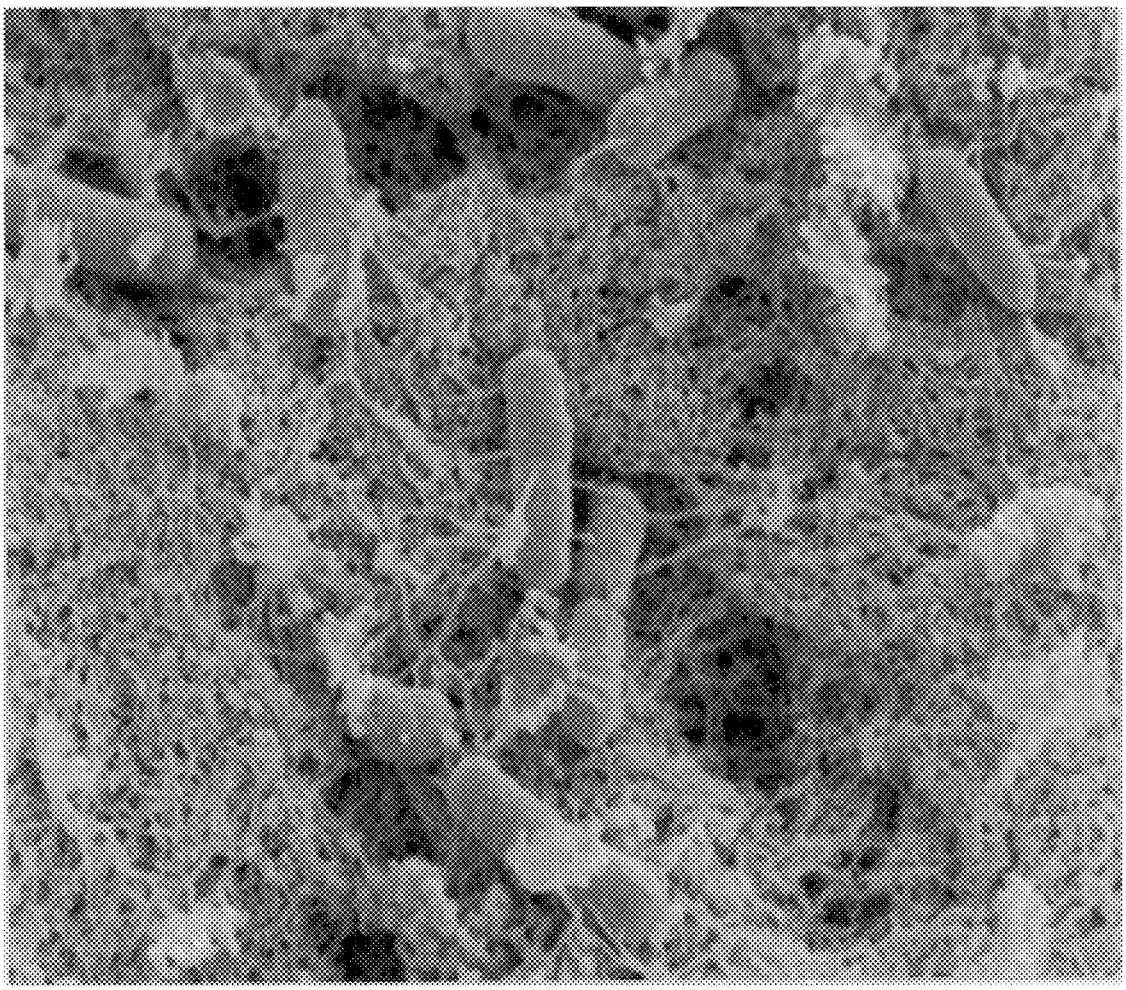
Figure 1H:
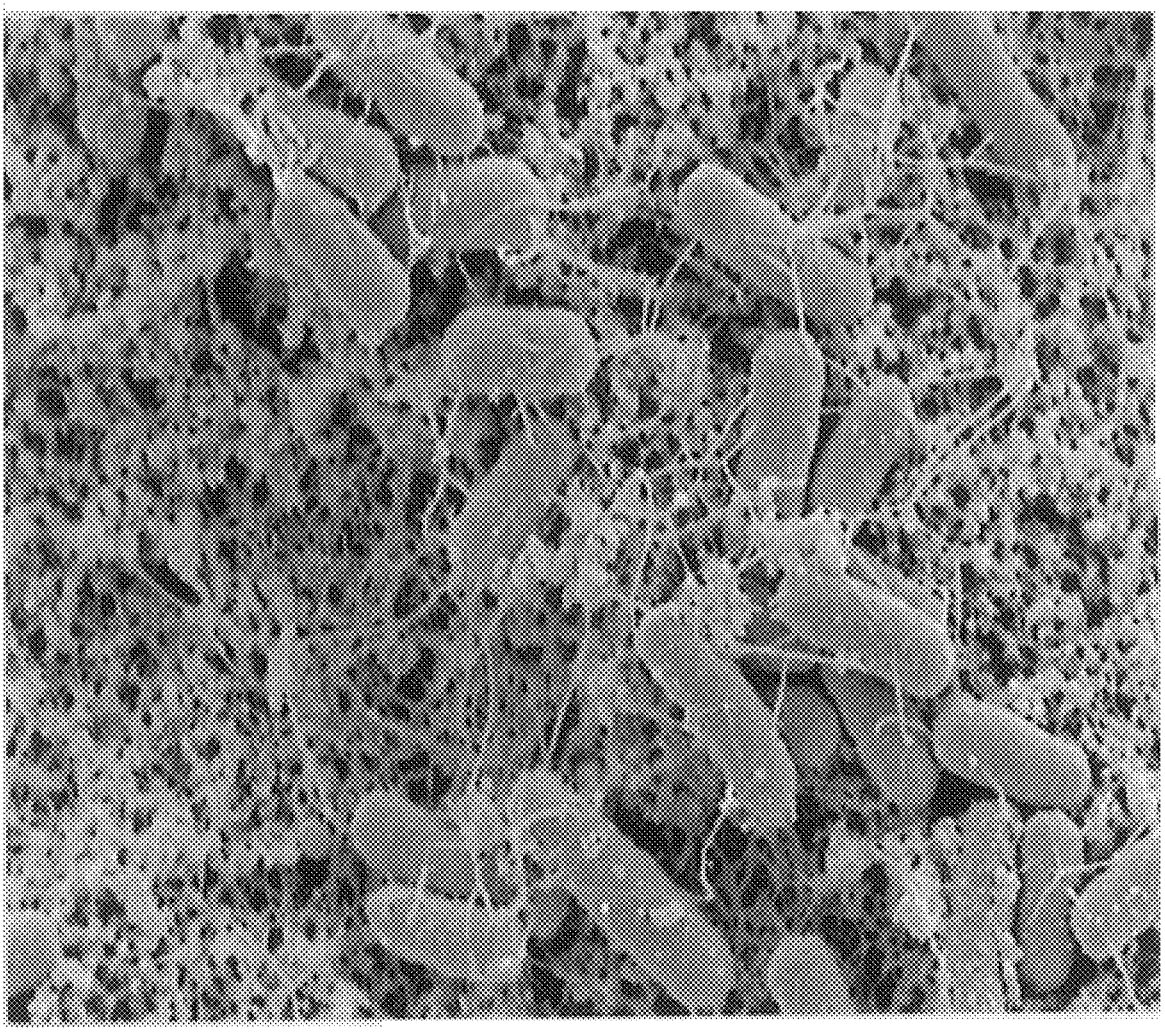
Figure 1I:
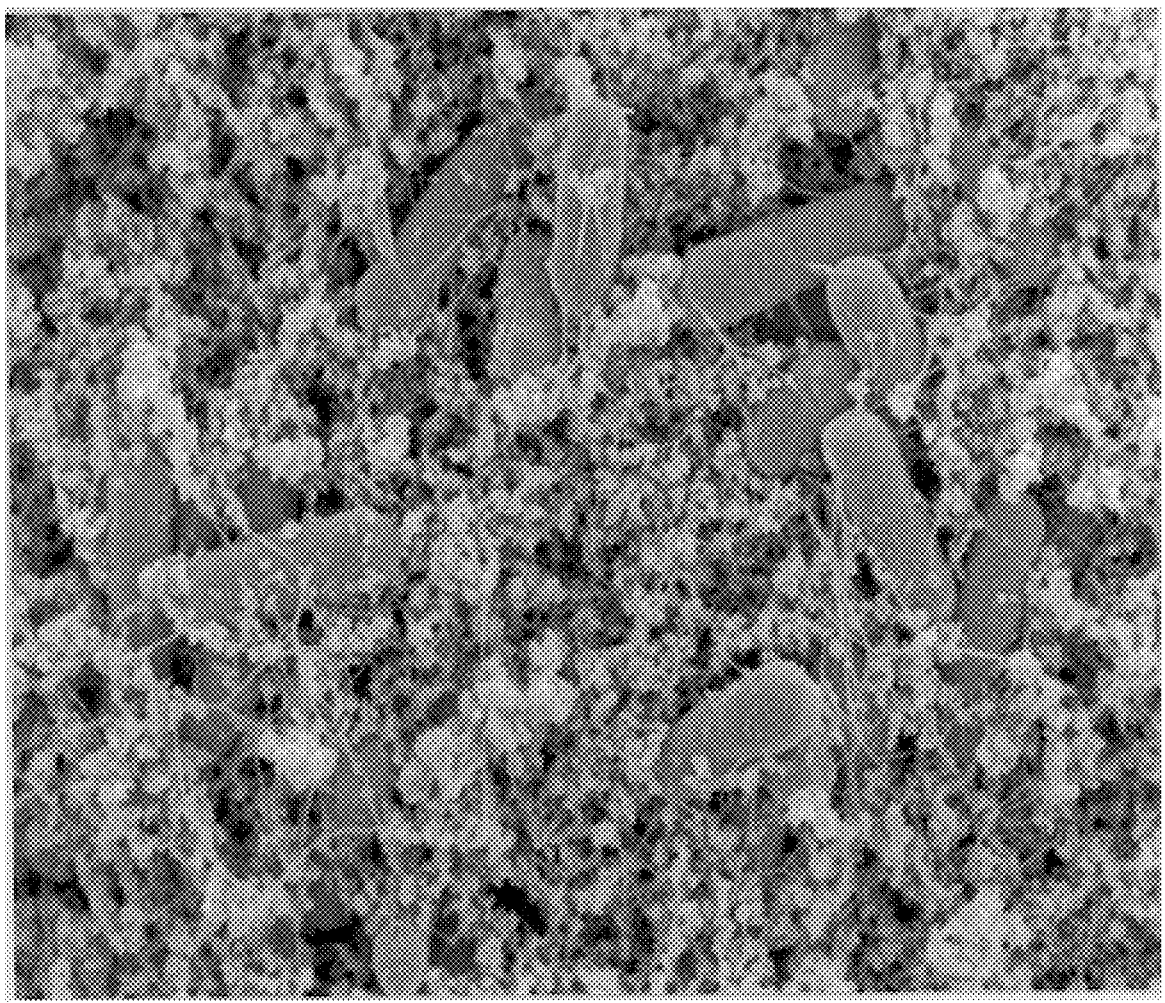
Figure 1J:
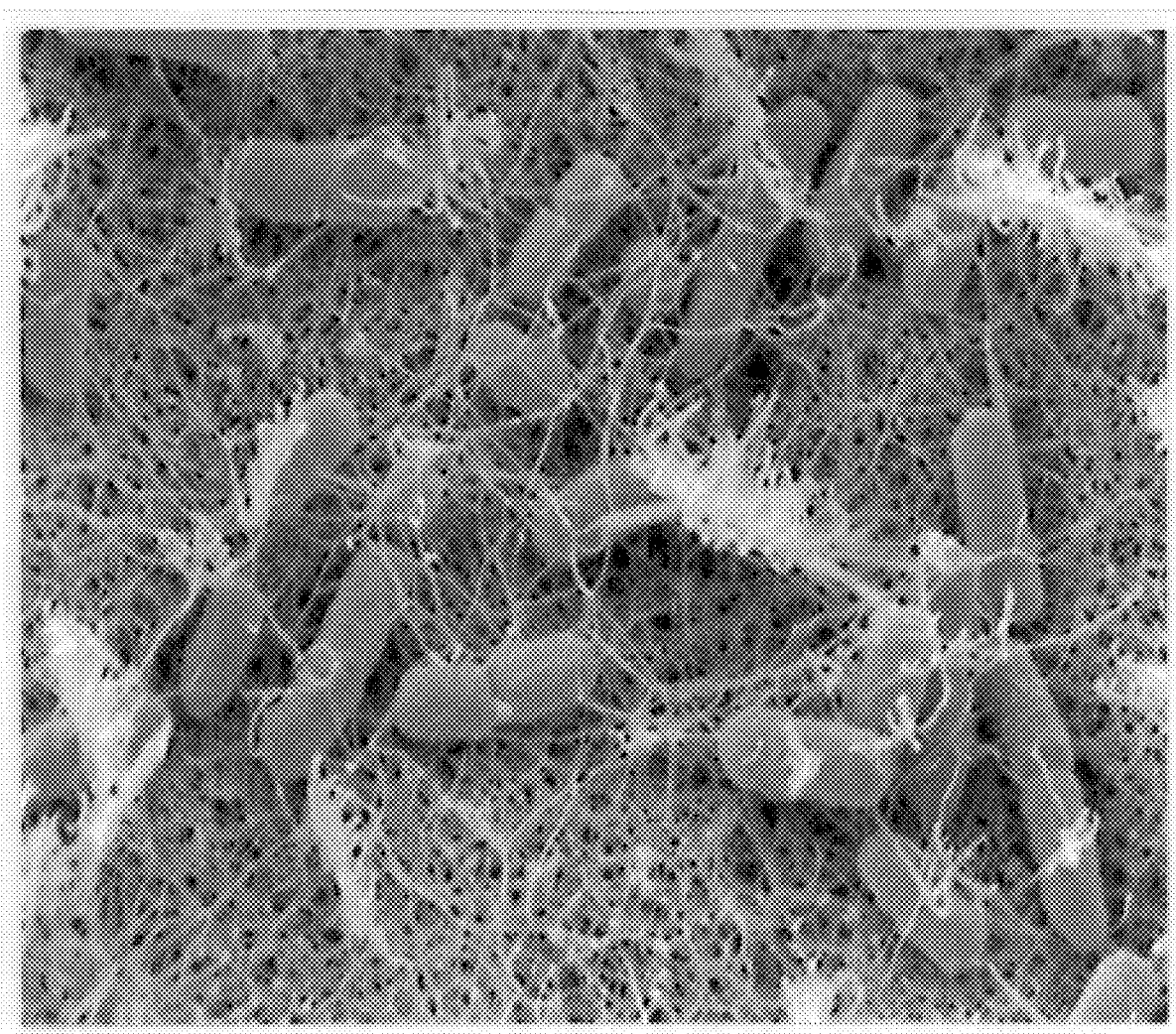
Figure 1K:
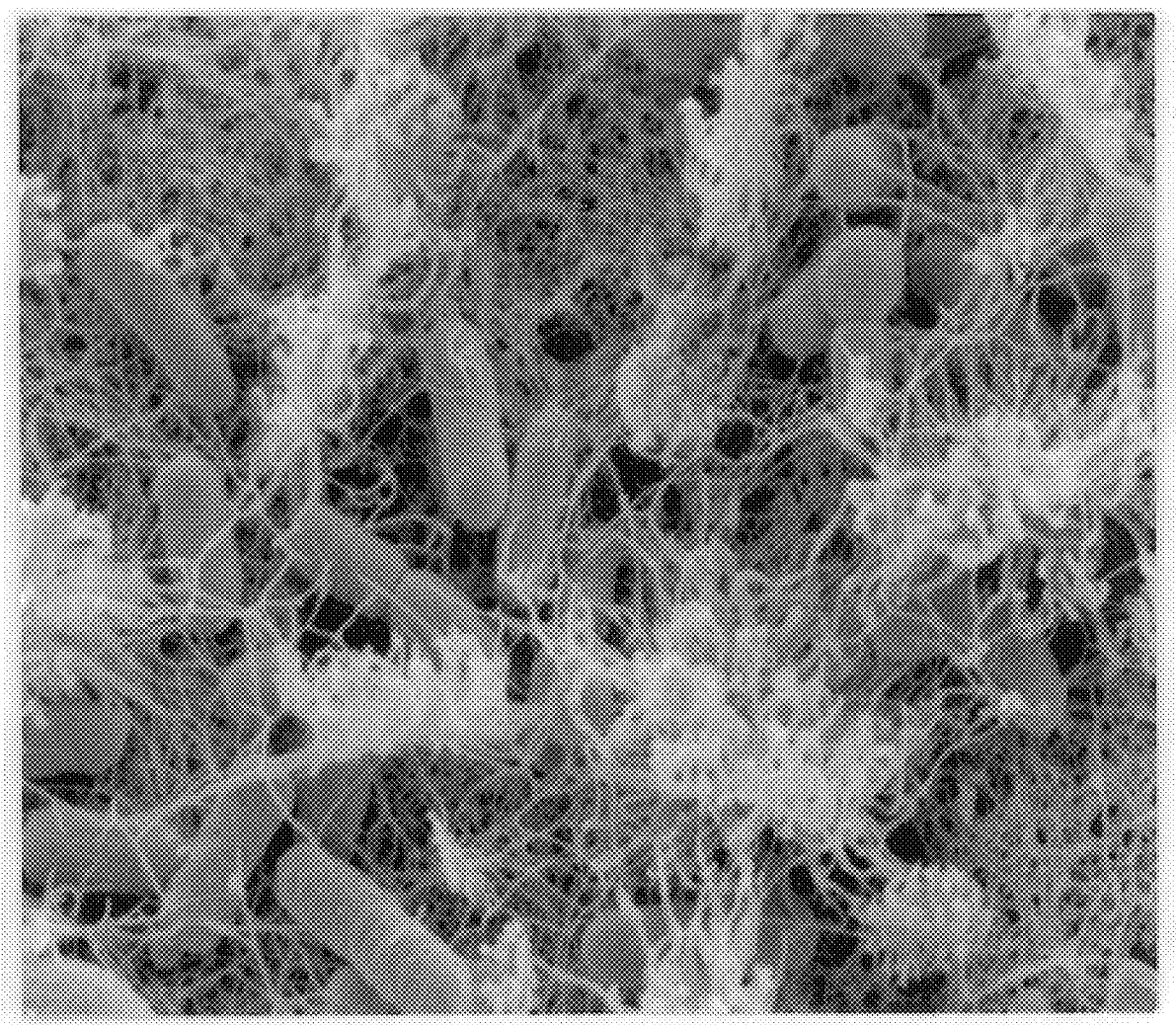

The morphology of cell surface appendages produced after supplementation depends on the formulation of the supplementation (FIGS. 1G–1K). Sometimes the cell surface changes are seen as blebs surrounding cells (FIGS. 1G–1I). Other times cell surface appendages were highly structured (FIGS. 1J–1K). Combination of two sugars, or of a sugar and an amino acid (FIGS. 1J and 1K) often produced more structure in cell surface appendages than single sugars and amino acids (FIGS. 1G–1I). Some combinations appear deleterious to differentiation. For example 100 mM maltose plus 10 mM glucose produced orange/yellow colonies on HEA, whereas 100 mM maltose plus 10 mM proline produced black colonies. Maltose alone at 100 mM produced yellow/orange colonies. Therefore, supplementation of sugars and amino acids in the presence of iron and reducing agents will allow identification of the metabolic pathways most conducive to the production of cell surface appendages. These findings make it possible to obtain desired types of cell surface changes by varying the formulation of the supplement.

Scanning electron microscopy (SEM) of Pullorum indicates that cells grown without 100 mM metabolite were short, misshaped and often lysed. Supplemented cells are rod-shaped, produced surface appendages and were less likely to lyse (FIGS. 2A and 2B). Supplementation of Enteritidis with 100 mM of the above listed metabolites produce dramatic hyperflagellation (FIGS. 2C and 2D). In addition to a peritrichous distribution, flagella sometimes formed bundles on cells when hyperflagellation occurred. Flagella within bundles are either "curly" or "rigid" (FIGS. 2D and 2E).

Surface flagellation is inducible in laboratory strains of Salmonella in brain heart infusion broth (BHI) (Difco) if 5 mM ferric ammonium citrate and 30 mM sodium thiosulfate is included in addition to a sugar, an amino acid or mixtures thereof. The iron and reducing agent are already present in HEA. It is also determined through the use of an iron chelator, 2,2-dipyridyl (Sigma), that unsupplemented BHI contains iron that improved culture yields two- to three-fold over that obtained from chelated broth (data not shown). However, iron and sodium thiosulfate by themselves, and higher concentrations of iron, up to 40 mM, did not result in differentiation without the inclusion of a sugar, an amino acid or mixtures thereof.

Variations exist in the response of different serovars and strains of a single serovar to supplementation especially in broth. In general, broth supplementation with either glucose or maltose at 10 mM or 100 mM is a sufficient range of metabolites to identify conditions that enhance flagellation (FIG. 3). Flagellin recovered from cells grown in broth is detected in polyacrylamide gels at 60, 54 and 50 kDa. N-terminal amino acid sequencing confirms that all three bands have the conserved Salmonella fliC N-terminus, (J. Li, et al., J. of Med. Microbiol., v. 38, pp. 129–139, 1993; Li et al., PNAS, USA, vol. 91, pp. 2552–2556, 1994) and thus these molecules are isotypes of flagellin. The 60 kDa isotype is the most common recovered from the cell surface of the three strains of Pullorum obtained from chickens and eggs as described in Example 1, although one condition is identified that yields the 50 kDa isotype in one of three strains (FIG. 3). Isotypes 60 and 54 kDa are recovered from a rough strain of Enteritidis, whereas little of the 50 kDa isotype could be detected in Coomasie stained polyacrylamide gels (FIG. 3). The 60 and 50 kDa isotypes are the most prevalent isotypes recovered from Typhimurium (FIG. 3). A smooth strain of Enteritidis was the only serovar to produce copious amounts of the 54 kDa isotype (FIG. 3). These results indicate that the prevalence of flagellar isotypes varied in response to environmental conditions in broth.

Although there is a small chance that the 60 kDa flagellin isotype is transcribed from a different gene than fliC, it is more probable that the electrophoretic differences between flagellin isotypes are due to interactions with charge and molecular weight variants of smooth lipopolysaccharide. Monoclonal antibodies were previously used to describe an intermolecular interaction between the 60 kDa flagellin isotype with smooth lipopolysaccharide (Guard-Petter et al, 1996, supra) whereas a polyclonal antiserum is required here to detect all three of the flagellin isotypes. The only commonly encountered non-stoichiometric modification to LPS that is known to increase the number of negative charges is phosphorylation. Mutants in the phosphorylating enzyme RfaP have been shown by others to affect the activity of outer membrane proteins as well as the structure of lipopolysaccharide (Parker et al, J. Bacteriol., volume 174, 2525–2538, 1992; Schnaitman et al, Microbiol. Rev., Volume 57, 655–682, 1993; Reeves, Biosynthesis and assembly of lipopolysaccharide. In Bacterial Cell Wall, Ghysen et al (Eds.), Volume 27, Chap. 13, 281–317, 1994; Stanley et al, Mol. Microbiol., Volume 10, 781–788, 1993). Pullorum is non-motile in standard sort-agar motility assays which suggests that the 60 kDa isotype might not contribute to motility. In other studies, the appearance of the 60 kDa isotype in Enteritidis is associated with an enhanced ability of cells to withstand environmental insults such as heat, acid and oxidizing reagents (Guard-Petter et al, 1996, supra; Humphrey et al, Epidemiology and Infection, 1996, In Press). The 54 kDa isotype has been most associated in Enteritidis with the ability to swarm and to produce copious amounts of peritrichous flagella (Guard-Petter et al, 1996, supra). A possible role for the 50 kDa isotype is that it might contribute to the formation of aggregated flagellar structures that are associated with invasiveness of the mucosal epithelium. In any case, it is possible that host-adapted Pullorum requires additional signals for differentiation from the chicken itself in order to finish its development in vivo.

Cell lysis is a prominent feature of Pullorum growth on HEA without supplementation. A 24 kDa protein was identified previously as a differentially expressed molecule produced by hyperflagellating cells that survived heat stress in the presence of complement (Guard-Petter, 1996, supra). This protein is detected again after supplementation of Enteritidis that produced hyperflagellation and the 54 kDa isotype. N-terminal sequencing of the first 20 amino acids of this protein identified it as AhpC (100% homology to var. Typhimurium and *E. coli* AhpC) which is a component of the alkyl hydrogen peroxide reductase enzyme system (Tarataglia et al, J. Biol. Chem., Volume 265, 10535–10540, 1990; Smillie et al, Genbank submission NCBL gi; 216542, 1993). Since this system scavenges oxygen and its derivatives, it is probable that oxidative stress is an immediate threat to the survival of differentiating cells of Salmonella, especially Pullorum. The flavoenzyme AhpF is a component of the same oxygen response enzyme (ORE) system as AhpC and might be the source of the striking yellow color of colonies. Oxygen stress responses involving AhpC homologs are highly conserved in bacteria, yeast, parasites and possibly even vertebrates (Chae et al, J. Biol. Chem., Volume 269, 27670–27678, 1994; Tsuji et al, Biochem. J., Volume 307, 377–381, 1995; Armstrong-Buisseret et al, Microbiology-UK, Volume 141, 1655–1661, 1995; Bruchhaus et al, Molecular and Biochemical Parasitology, Volume 70, 187–191, 1995; Ferrante et al, PNAS, USA, Volume 92, 7617–7621,1995; Wilson et al, Mol. Microbiol., Volume 19, 1025–1034, 1996) which suggests that these OREs are a common denominator in the process of cellular differentiation. In prokaryotes such responses are under the global regulation of OxyR (Storz et al, J. Nutrition, Volume 122, 627–630,1992; Park et al, J. Bacteriol., Volume 177, 6255–6262, 1995). Therefore, a possible mechanism by which growth supplementation aids differentiation is that it relieves oxidative stress encountered when global changes occur in the outer membrane.

EXAMPLE 3

Clinical diagnosis of salmonellosis always includes flagellin H-antigen serotyping in addition to lipopolysaccharide (LPS) O-antigen serotyping. To see how growth on HEA with supplementation affected the detection of H-antigens, salmonellae O-antigen serotypes B, C1, C3, E1, E4 and G2 were grown with 100 mM glucose supplementation on HEA plates at 37° C. for 16 hours (40 hours for Pullorum). Isolates were confirmed to have typical slide agglutination reactions by using diagnostic antiserum and by submitting selected isolates for independent identification to the National Veterinary Services Laboratory (Ames, Iowa). Results are that many of the H-antigen serotype differences between the salmonellae using polyclonal antisera G-complex, poly a-z and poly B are abolished when strains are grown with supplementation (Table 1). Antiserum EN did not react with var. Braenderup and var. Anatum as was expected, while it gave an unexpected positive reaction with var. Schwarzengund. Even single factor reactivity was altered. For example, var. Typhimurium

TABLE 1

H-antigen slide agglutination reactivity of non-D-1
O-antigen Salmonella Grown under inducing conditions (100 mM Glucose)

| | | Diagnostic Antiserum | | | | | | | | | |
|---|---|---|---|---|---|---|---|---|---|---|---|
| Strain | (Serovar) | G-complex | EN | poly a-z | poly B | poly C | poly D | factor 2 | factor 5 | factor 6 | factor 7 |
| S. typhimurium-LT2 | (B) | + | − | + | + | − | − | + | − | − | + |
| S. typhimurium | (B) | + | − | + | + | − | − | + | − | − | + |
| S. schwarzengund | (B) | + | + | + | + | − | + | + | + | − | + |
| S. oranienburg | (C1) | + | − | + | + | + | + | − | − | + | − |
| S. braenderup | (C1) | − | − | + | + | − | + | − | + | − | − |
| S. thompson | (C1) | + | − | + | + | − | + | + | + | + | + |
| S. kentucky | (C3) | + | − | + | + | − | − | − | − | − | − |
| S. anatum | (E1) | − | − | + | + | + | + | − | + | + | − |
| S. senftenburg | (E4) | + | − | + | + | + | + | − | − | + | − |
| S. worthington | (G2) | − | − | + | + | + | + | + | − | − | − |

TABLE 2

H-antigen slide agglutination reactivity of
Serovar D-1 O-antigen Salmonellae

| | | Diagnostic antiserum | | | | | | | | | |
|---|---|---|---|---|---|---|---|---|---|---|---|
| Strain | (number of isolates tested) | G-complex | EN | poly a-z | poly B | poly C | poly D | factor 2 | factor 5 | factor 6 | factor 7 |
| S. pullorum | 4 | + | − | + | + | var[1] | var | var | var | var | var |
| S. enteritidis, pt 23[2] | 4 | + | − | + | + | var | var | var | var | var | var |
| S. enteritidis, pt 13a[3] | 6 | + | − | + | + | − | var | var | var | var | var |
| S. enteritidis, pt 13a[4] | 5 | + | var | + | + | − | − | var | − | − | − |
| S. enteritidis, pt 8 | 3 | + | var | + | + | − | − | var | − | − | − |
| S. enteritidis, pt 4 | 9 | + | − | + | + | − | − | var | − | − | − |
| S. berta | 1 | + | − | + | + | − | − | − | − | − | − |
| S. rostock | 1 | + | − | + | + | − | − | + | − | − | − |
| S. wanagata | 1 | + | − | + | + | − | − | − | − | − | − |
| S. portland | 1 | + | + | + | + | − | − | + | − | − | − |
| S. dublin | 1 | + | − | + | + | − | − | − | − | − | − |
| S. pensacola | 1 | + | − | + | + | − | − | + | − | − | − |
| S. heidelburg | 1 | + | + | + | + | − | − | + | − | − | − |
| S. javiana | 1 | + | − | + | + | − | − | + | − | − | − |
| S. johannesburg | 1 | + | + | + | + | − | + | − | − | − | − |
| S. napoli | 1 | + | − | + | + | + | − | + | − | − | − |

[1] variable reaction between isolates
[2] rough phenotype, lacks O-antigen without metabolite supplementation on HEA
[3] virulent smooth isogenic variant of rough phenotype
[4] virulent smooth isogenic variant of rough phenotype does not usually react with factor 7, var. Thompson does not usually react with factors 2, 6 and 7; and var. Senftenberg does not usually react with factor 6. Enteritidis immunoreactivity was dependent on phage type (Table 2) and phage types 4, 8 and virulent strains of pt 13A were less reactive to H-antigen factors 5, 6 and 7 than were rough and avirulent pt 13A strains. Other D1 serovars not associated with contamination of eggs lacked immunoreactivity with factors 5, 6 and 7, whereas Pullorum immunoreactivity closely resembled that of less virulent strains of Enteritidis. These results indicate that considerable flagellin epitope variation exists even between isogenic variants of a single serovar, whereas other epitopes are conserved between serovars. These findings are in agreement with the fliC gene arrangement, where N- and C-terminal regions are highly conserved among enteric organisms and the middle region is highly variable (MacNab, Ann. Rev. Genet., Volume 26, 131–158, 1992; Raha et al, J. Gen. Microbiol., Volume 139, 1401–1407, 1993; Kilger et al, J. Clin. Microbiol., Volume 31, 1108–1110, 1993; all herein incorporated by reference).

EXAMPLE 4

Figure 4A:
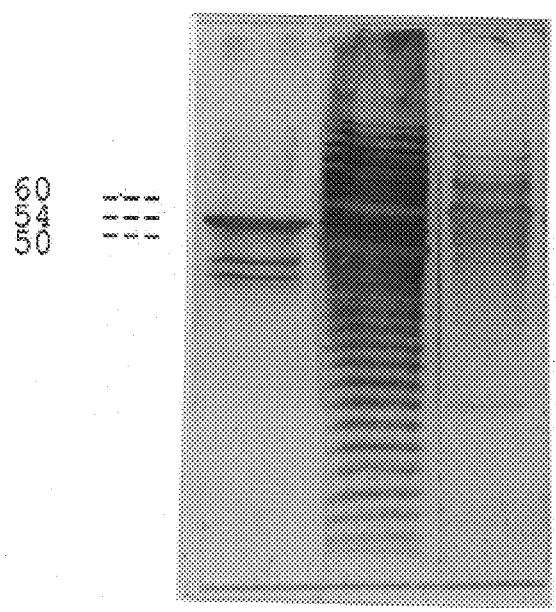
FIGS. 4A and 4B are photographs of a polyacrylamide gel showing H- and O-antigen immunoreactivity of salmonellae flagellin after metabolite supplementation.
Figure 4B:
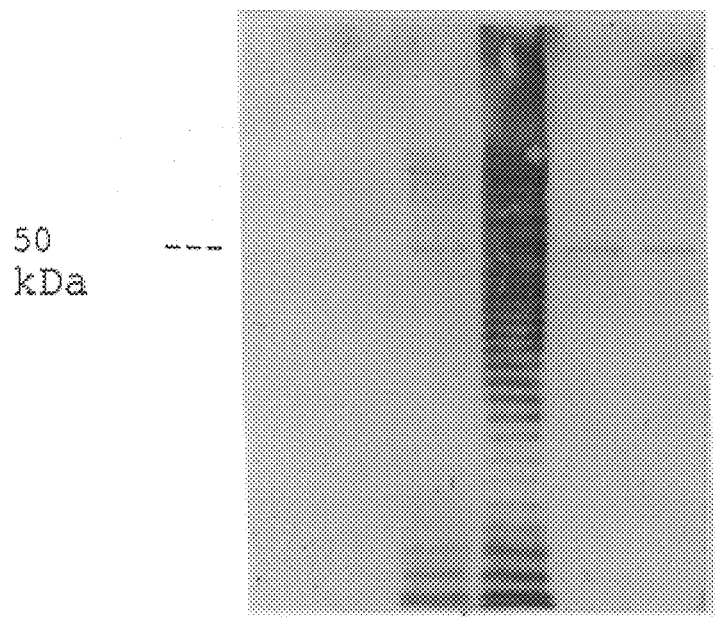

A molecular basis for the cross-reactivity of H-antigens appears to be an interaction between lipopolysaccharide and flagellin. To investigate this interaction, ammonium sulfate precipitated cell surface material recovered from vortexed cells is immunoblotted using flagellin H-antigen typing antisera G-complex, poly B and poly a-z as primary antisera. Primary antisera is diluted 1:250 in phosphate buffered saline (PBS) and secondary antibody is goat anti-rabbit alkaline phosphate labeled IgG (Pierce) diluted 1:2500. Samples are transferred to nitrocellulose membranes from 10% to 16% polyacrylamide gels prepared according to standard techniques (Laemmli, Nature, Volume 227, 680–685, 1970; Towbin et al PNAS, USA, Volume 76, 4350–4354, 1979, 19; herein incorporated by reference). Typhimurium LT2, Enteritidis, and Pullorum were cultured on HEA at 37° C. for 16 hours (40 hours for Pullorum) supplemented with either 100 mM glucose, 10 mM maltose or 100 mM maltose. Similar results are obtained from all three antisera and show that 1) metabolite supplementation results in detection of an LPS O-antigen ladder for a rough Enteritidis and smooth Pullorum, but not serovar B Typhimurium; 2) metabolite supplementation results in detection of 60 and 50 kDa flagellin isotypes but they often appear as negative or masked bands on immunoblots, and 3) a 54 kDa flagellin band is detectable as a positive band for group B and D1 serovars (FIG. 4A). In addition to H-antigen serotyping, D1 O-antigen antiserum is used for immunoblotting. As expected, an O-antigen ladder was detected for homologous smooth Enteritidis that was not detected for heterologous Typhimurium and rough Enteritidis. However, an unexpected result was that D1 O-antigen detected the 50 kDa flagellin isotype of smooth and rough Enteritidis (FIG. 4B). The rough strain in these studies was isogenic to smooth Enteritidis and had seroconverted to a positive D1 O-antigen slide agglutination reaction when it was supplemented. Thus metabolite supplementation enhances production of smooth LPS which forms an association with flagella that affects the immunoreactivity of both molecules.

The foregoing detailed description is for the purpose of illustration. Such detail is solely for that purpose and those skilled in the art can make variations therein without departing from the spirit and scope of the invention.

We claim:

1. A culture medium growth supplement consisting essentially of (a) an effective amount of a metabolite selected from the group consisting of sugars, free amino acids, and mixtures thereof for inducing differentiation and/or maintaining differentiation of bacterial cells, (b) an iron-containing compound, and (c) about 20 mM to about 40 mM of a reducing agent;

wherein said supplement when added to a bacterial culture medium, causes bacteria to hypersecrete proteins when cultured with said supplemented medium.

2. The supplement of claim 1 wherein said metabolite is sugars and said effective amount of said sugar is in the range of about 1 mM to about 100 mM.

3. The supplement of claim 2 wherein said effective amount of said sugar is in the range of about 10 mM to about 100 mM.

4. The supplement of claim 1 wherein the metabolite is selected from the group consisting of glucose, maltose, proline, glutamine, N-acetylglucosamine, glucosamine and mixtures thereof.

5. A method for inducing differentiation and maintaining viability of bacterial cells in culture comprising providing a bacterial culture medium containing a growth supplement, wherein the growth supplement consists essentially of a metabolite selected from the group consisting of sugars, free amino acids, and mixtures thereof in amounts effective to induce and/or maintain differentiation of said bacterial cells; an iron-containing compound; and about 20mM to about 40 mM of a reducing agent; and incubating bacterial cells in said supplemented medium wherein said bacterial cells hypersecrete proteins.

6. The method of claim 5 wherein inducing differentiation comprises flagellation of aflagellate bacteria.

7. The method of claim 5 wherein the metabolite is selected from the group consisting of glucose, maltose, proline, glutamine, N-acetylglucosamine, glucosamine and mixtures thereof.

* * * * *